US011567151B2

(12) United States Patent
Liu et al.

(10) Patent No.: US 11,567,151 B2
(45) Date of Patent: Jan. 31, 2023

(54) POSITIONING APPARATUS FOR MAGNETIC RESONANCE IMAGING

(71) Applicant: OUR UNITED CORPORATION, Xi'an (CN)

(72) Inventors: Hui Liu, Xi'an (CN); Song Liu, Xi'an (CN); Daliang Li, Xi'an (CN)

(73) Assignee: OUR UNITED CORPORATION, Xi'an (CN)

( * ) Notice: Subject to any disclaimer, the term of this patent is extended or adjusted under 35 U.S.C. 154(b) by 0 days.

(21) Appl. No.: 17/527,594

(22) Filed: Nov. 16, 2021

(65) Prior Publication Data
US 2022/0155388 A1    May 19, 2022

(30) Foreign Application Priority Data
Nov. 16, 2020  (CN) .......................... 202022652610.3

(51) Int. Cl.
*G01R 33/30*       (2006.01)
(52) U.S. Cl.
CPC ................... *G01R 33/307* (2013.01)
(58) Field of Classification Search
CPC .. G01R 33/307; G01R 33/4808; G01R 33/30; G01R 33/58; A61N 2005/1055
See application file for complete search history.

(56) References Cited

U.S. PATENT DOCUMENTS 5,005,578 A * 4/1991 Greer ..................... G01R 33/58
324/318

FOREIGN PATENT DOCUMENTS

| CN | 2678590 Y * | 3/2004 | ............. A61B 19/00 |
| CN | 2678590 | 2/2005 | |
| CN | 211215043 | 8/2020 | |
| WO | WO-2006134357 A1 * | 12/2006 | ............. G01R 33/28 |

OTHER PUBLICATIONS

Machine Translation of CN-2678590 (Year: 2004).*

* cited by examiner

*Primary Examiner* — G. M. A Hyder
(74) *Attorney, Agent, or Firm* — Emerson, Thomson & Bennett, LLC; Roger D. Emerson; Warren A. Rosborough

(57) ABSTRACT

Embodiments of the present disclosure provide a positioning apparatus for magnetic resonance imaging, including a three-dimensional frame structure formed by marking plate assemblies. The marking plate assemblies include an inner marking plate, an outer marking plate arranged opposite to the inner marking plate, and an image developing tube in which a developer solution is enclosed, opposite surfaces of the inner marking plate and the outer marking plate are respectively provided with groove structures, the image developing tube is arranged in a cavity formed by the groove structure in the inner marking plate and the groove structure in the outer marking plate, and the number of the marking plate assemblies is greater than or equal to 4.

16 Claims, 3 Drawing Sheets

POSITIONING APPARATUS FOR MAGNETIC RESONANCE IMAGING

CROSS-REFERENCE TO RELATED APPLICATIONS

This disclosure claims the priority to CN 202022652610.3 filed on Nov. 16, 2021, which is hereby incorporated by reference in its entirety.

TECHNICAL FIELD

Embodiments of the present disclosure relate to the technical field of medical equipment, in particular to a positioning apparatus for magnetic resonance imaging (MRI).

BACKGROUND

When performing MRI radiation therapy on a head tumor of a patient, it is necessary to accurately locate the intracranial tumor, so that the patient needs to have a relatively accurate position in a positioning status. However, in actual use, due to the presence of various errors such as positioning error or error of a movable couch itself, there is deviations in MRI images, and precise positioning of the tumor cannot be achieved.

SUMMARY

In view of this, one of the technical problems solved by embodiments of the present disclosure is to provide a positioning apparatus for MRI for overcoming all or part of the above-mentioned defects.

An embodiment of the present disclosure provides a positioning apparatus for MRI, including a three-dimensional frame structure formed by marking plate assemblies. The marking plate assemblies include an inner marking plate, an outer marking plate arranged opposite to the inner marking plate, and an image developing tube in which a developer solution is enclosed, opposite surfaces of the inner marking plate and the outer marking plate are respectively provided with groove structures, the image developing tube is arranged in a cavity formed by the groove structure in the inner marking plate and the groove structure in the outer marking plate, and the number of the marking plate assemblies is greater than or equal to 4.

Alternatively, in an embodiment of the present disclosure, the image developing tube is a plastic hose with a preset hardness, and the preset hardness ranges from 45A to 85A.

Alternatively, in an embodiment of the present disclosure, the preset hardness is 65A.

Alternatively, in an embodiment of the present disclosure, two ends of the image developing tube are respectively provided with plugs, and the plugs are sealed together with the image developing tube through a thermoplastic process.

Alternatively, in an embodiment of the present disclosure, at least one of the plugs is closely fitted in the image developing tube.

Alternatively, in an embodiment of the present disclosure, the inner marking plate and the outer marking plate are detachably connected.

Alternatively, in an embodiment of the present disclosure, the inner marking plate and the outer marking plate are connected by a fixing member with an outer thread.

Alternatively, in an embodiment of the present disclosure, the groove structure in the inner marking plate and the groove structure in the outer marking plate respectively include a groove arranged along an edge and a diagonal direction of the inner marking plate, and a groove arranged along an edge and a diagonal direction of the outer marking plate.

Alternatively, in an embodiment of the present disclosure, the groove structure further includes a groove extension part arranged along the diagonal direction at a position where the grooves intersect, and the image developing tube is bent at the position where the grooves intersect so that the two ends of the image developing tube are arranged in the groove extension part.

Alternatively, in an embodiment of the present disclosure, at least one first connecting hole is provided in a first region defined by intersecting grooves in the inner marking plate, at least one second connecting hole is provided in a second region defined by intersecting grooves in the outer marking plate, and each of the first and second connecting holes in the first and second regions is provided with an inner thread that fits with the outer thread of the fixing member.

Alternatively, in an embodiment of the present disclosure, the developer solution includes one of the following materials: a copper sulfate solution, glycerin, and a nitrate oil solution.

Alternatively, in an embodiment of the present disclosure, the marking plate assemblies include a straight upper marking plate assembly configured to cover a face of a patient when in use, a straight left marking plate assembly and a straight right marking plate assembly configured to respectively cover left and right ears of the patient when in use, and a straight front marking plate assembly configured to cover a top of a head of the patient when in use.

Alternatively, in an embodiment of the present disclosure, an inverted V-shaped opening is provided under the straight upper marking plate assembly.

Alternatively, in an embodiment of the present disclosure, the marking plate assemblies further include a lower marking plate assembly arranged in parallel with the straight upper marking plate assembly.

Alternatively, in an embodiment of the present disclosure, the three-dimensional frame structure further includes connecting plates, and the connecting plates are arranged between the straight front marking plate assembly and other marking plate assemblies for fixedly connecting the straight front marking plate assembly with the other marking plate assemblies.

Alternatively, in an embodiment of the present disclosure, each of the connecting plates has a cuboid structure, and a through hole is provided at a center position of the connecting plate.

In the positioning apparatus for MRI provided in the embodiment of the present disclosure, since the developer solution is enclosed in the image developing tube, the image developing tube is arranged in the cavity formed by the inner marking plate and the outer marking plate, the positioning apparatus for MRI will not leak the developer solution even though the inner marking plate or the outer marking plate does not meet the process requirements, which improves the use performance of the positioning apparatus for MRI.

BRIEF DESCRIPTION OF THE DRAWINGS

Hereinafter, some specific embodiments of the embodiments of the present disclosure will be described in detail in an exemplary but not restrictive method with reference to the accompanying drawings. The same reference numerals in the accompanying drawings indicate the same or similar components or parts. Those skilled in the art should appreciate that these accompanying drawings are not necessarily drawn to scale. In the accompanying drawings.

DETAILED DESCRIPTION OF EMBODIMENTS

In order to eliminate MRI errors, an external N-shaped developing line is usually used for positioning. In a related art, inner and outer plates provided with N-shaped linear grooves are used for bonding, and a developer solution is poured into the bonded N-shaped linear grooves to form a fixing plate. When performing an MRI scan on the head of the patient, such three fixing plates are set around the head of the patient. After scanning using an MRI equipment, several positioning points for measuring errors may be displayed on a tomographic image, and relative coordinate changes of these positioning points are used to determine the magnitude of the errors in the current status. However, in this art, if there is a deviation in the manufacturing process of the inner and outer plates, there may be a gap after the inner and outer plates are bonded, resulting in leakage of a developing agent during use. The leakage of the developing agent may cause bubbles to be generated in the N-shaped linear grooves, affecting the use performance of the apparatus.

The specific implementation of embodiments of the present disclosure will be further described below in conjunction with the accompanying drawings of the embodiments of the present disclosure.

The terms used in the present disclosure are only for the purpose of describing specific embodiments, and are not intended to limit the present disclosure. The singular forms of "a", "the" and "this" used in the present disclosure and the appended claims are also intended to include plural forms, unless the context clearly indicates other meanings. It should also be understood that the term "and/or" as used herein refers to and includes any or all possible combinations of one or more associated listed items.

It should be understood that the "first", "second" and similar words used in the specification and claims of the present disclosure do not indicate any order, quantity or importance, but are only used to distinguish different components. Similarly, similar words such as "a" or "an" do not indicate a quantity limit, but indicate that there is at least one. Unless otherwise indicated, similar words such as "front", "rear", "lower" and/or "upper" are only for convenience of description, and are not limited to a position or a spatial orientation. "Include" or "contain" and other similar words mean that the elements or items before "include" or "contain" cover the elements or items listed after "include" or "contain" and their equivalents, and do not exclude other elements or items. Similar words such as "connected" or "linked" are not limited to physical or mechanical connections, and may include electrical connections, whether direct or indirect.

The specific implementation of the embodiments of the present disclosure will be further described below in conjunction with the accompanying drawings of the embodiments of the present disclosure.

Figure 1:
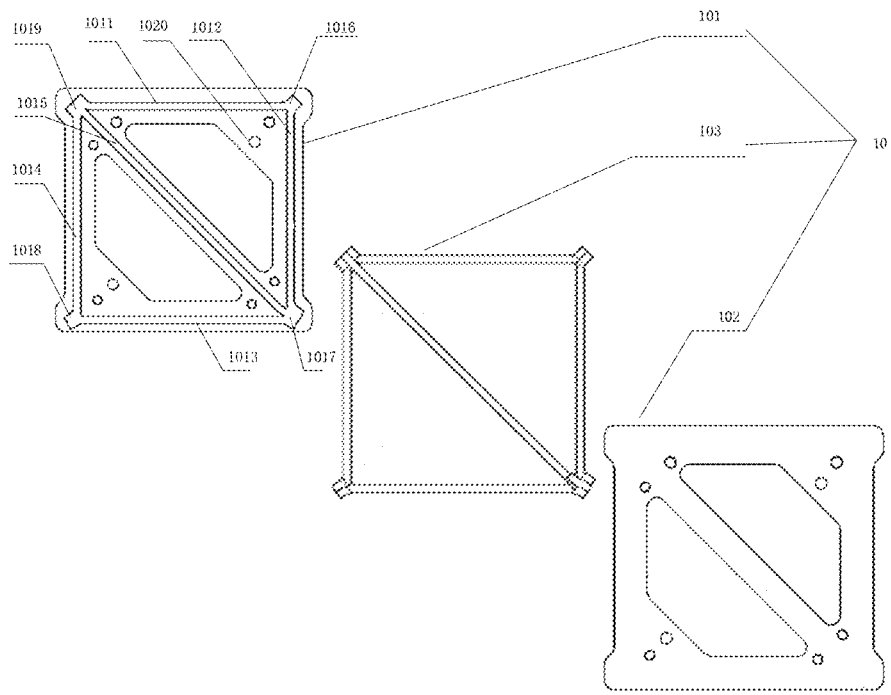
FIG. 1 is a schematic diagram of an exploded structure of a marking plate assembly provided in an embodiment of the present disclosure.

FIG. 1 is a schematic diagram of an exploded structure of a marking plate assembly provided by an embodiment of the present disclosure. As shown in FIG. 1, the marking plate assembly 10 may include an inner marking plate 101, an outer marking plate 102 arranged opposite to the inner marking plate 101, and an image developing tube 103 in which a developer solution is enclosed. Opposite surfaces of the inner marking plate 101 and the outer marking plate 102 are respectively provided with groove structures, and the image developing tube is arranged in a cavity formed by the groove structure in the inner marking plate 101 and the groove structure in the outer marking plate.

Figure 2:
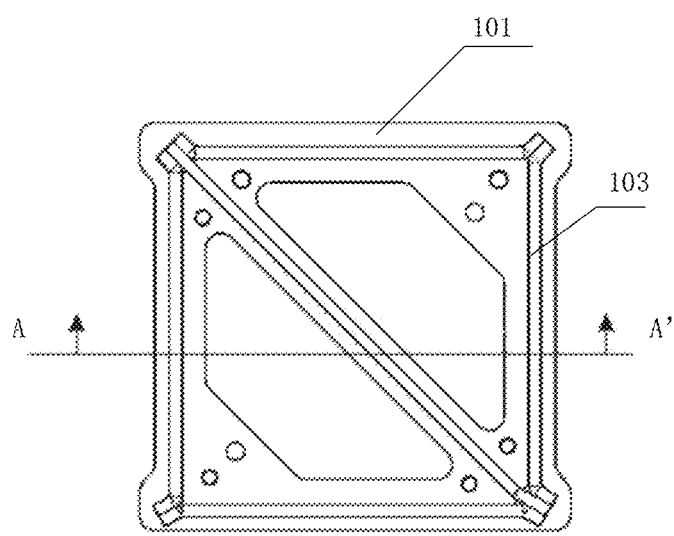
FIG. 2 is a schematic diagram of a structure of an inner marking plate equipped with an image developing tube provided in an embodiment of the present disclosure.
Figure 3:
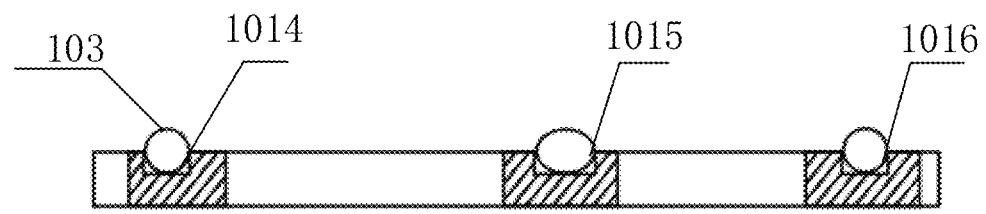
FIG. 3 is a cross-sectional view of the inner marking plate shown in FIG. 2 taken along A-A'.

As shown in FIG. 2 and FIG. 3, when the image developing tube 103 is placed in the groove structure in the inner marking plate 101, a part of the image developing tube 103 protrudes from the groove structure to be accommodated in the groove structure in the outer marking plate 102, when the outer marking plate 102 and the inner marking plate 101 are connected. It should be noted that in the present embodiment, the structures of the outer marking plate 102 and the inner marking plate 101 are mirror-symmetrical. In order to avoid redundant description, the inner marking plate 101 is used for detailed description below. It should be understood that all structures suitable for the inner marking plate 101 are suitable for the outer marking plate 102.

In the marking plate assembly provided in the present embodiment, since the developer solution is enclosed in the image developing tube, the image developing tube is arranged in the cavity formed by the inner marking plate and the outer marking plate, the marking plate assembly will not leak the developer solution even though the inner marking plate or the outer marking plate does not meet the process requirements. For example, there will be no gap between the inner marking plate and the outer marking plate after assembly of the inner marking plate and the outer marking plate due to deviations in the manufacturing process, so that the developer solution leaks out of the gap and affecting use of the marking plate assembly.

In the present embodiment, the developer solution may include one of the following materials: a copper sulfate solution, glycerin, and a nitrate oil solution. The developer solution may also be other imaging marking materials for magnetic resonance imaging, which is not limited in the present embodiment.

In order to prevent the developer solution leaking from the image developing tube 103 and causing bubbles in the developing tube, which cannot meet the usage requirements, alternatively, the image developing tube 103 may be a plastic hose with a preset hardness. The preset hardness may range from 45A to 85A, preferably 65A. According to the actual encapsulating situation, when the Rockwell hardness of the image developing tube 103 is within the preset hardness range, especially at about 65A, the developer solution enclosed in the image developing tube 103 is not prone to leak.

In the present embodiment, the image developing tube 103 may be sealed through a thermoplastic process to encapsulate the developer solution in the image developing tube 103. Alternatively, in an implementation, two ends of the image developing tube 103 are respectively provided with plugs (not shown), and the plugs are sealed together with the image developing tube 103 through the thermoplastic process.

For example, when encapsulating, first, one end of the image developing tube 103 is inserted into a plug, and a gap between the plug and the image developing tube 103 is filled through the thermoplastic process using a thermoplastic machine. Then, a syringe is used to connect a capillary tube deep into the bottom of the image developing tube 103, and the developer solution (such as copper sulfate solution) is injected from the bottom of the image developing tube 103 to ensure that no bubbles are generated at the bottom of the image developing tube 103. Since the capillaries occupy a part of an internal volume of the image developing tube 103, the capillaries need to be slowly drawn out while the developer solution is injected until the developer solution fills the entire image developing tube 103. After the image developing tube 103 is filled, a plug is inserted into the other end of the image developing tube 103, and then sealed through the thermoplastic process to encapsulate the developer solution in the image developing tube 103.

In the process of sealing the gap between the plug and the image developing tube 103 through the thermoplastic process after filling the image developing tube 103, in order to avoid that the gap between the plug and the image developing tube 103 is too large, the developer solution directly contacts a high-temperature heat source and vaporizes instantaneously when sealed through the thermoplastic process, so that the image developing tube is filled with a large number of bubbles and cannot meet the usage requirements, alternatively, the plug inserted after filling the image developing tube 103 closely fits in the image developing tube 103, thereby preventing the developer solution from directly contacting the high-temperature heat source through the gap between the plug and an inner wall of the image developing tube 103, so as to avoid the image developing tube 103 being filled with bubbles due to instant vaporization of the developer solution, which cannot meet the usage requirements.

Alternatively, in order to further ensure that the developer solution does not instantly vaporize due to the high-temperature heat source, alternatively, a length of the plug inserted into the image developing tube 103 after filling the image developing tube 103 is greater than a preset length. The preset length is the minimum length to prevent the instant vaporization of the developer solution due to the proximity of the high-temperature heat source.

Alternatively, in an embodiment of the present disclosure, the inner marking plate 101 and the outer marking plate 102 are detachably connected. Compared with the related art, the inner marking plate 101 and the outer marking plate 102 are connected by bonding, this connection method (detachably connected method) may realize an effective disassembly of the inner marking plate 101 and the outer marking plate, avoiding parts (for example, the inner marking plate 101 and the outer marking plate) damage during the disassembly.

For example, in a specific implementation, the inner marking plate 101 and the outer marking plate 102 may be connected by a threaded fixing member (not shown), such as by screw connection. This makes it possible to modify the connection of the inner marking plate 101 and the outer marking plate in real time by adjusting the fixing member, such as by adjusting the screw, if it is found that the connection between the inner marking plate 101 and the outer marking plate 102 does not meet the process requirements during use, avoiding the problem that unqualified parts are difficult to modify.

Alternatively, in the present embodiment, the groove structure in the inner marking plate 101 and the groove structure in the outer marking plate 102 may include a groove arranged along an edge and a diagonal direction of the inner marking plate 101, and a groove arranged along an edge and a diagonal direction of the outer marking plate 102, respectively. For example, as shown in FIG. 1, the groove structure in the inner marking plate 101 includes mutually connected grooves 1011-1015. The grooves 1011-1014 form a square. The groove 1015 is provided in the diagonal direction of the square. A trapezoidal through hole and its variation are respectively provided on two sides of the groove 1015 to reduce the weight of the marking plate assembly.

Alternatively, the groove structure may further include a groove extension part arranged along the diagonal direction at a position where the grooves intersect, and the image developing tube 103 is bent at the position where the grooves intersect so that the two ends of the image developing tube 103 are arranged in the groove extension part. Specifically, referring to FIG. 1, a groove extension part 1016 is provided at the intersection of the grooves 1011 and 1012, a groove extension part 1017 is provided at the intersection of the grooves 1012, 1013, and 1015, a groove extension part 1018 is provided at the intersection of the grooves 1013 and 1014, and a groove extension part 1019 is provided at the intersection of the grooves 1014, 1015, and 1011. By providing the groove extension parts, the ends of the image developing tube 103 are arranged in the groove extension parts by bending, which may facilitate fixing the image developing tube 103 in the groove structures.

Since the image developing tube 103 is bent at the position where the grooves intersect to be fixed in the groove extension parts, the image developing tube 103 is elastically deformed at the bend, and a restoring force may be generated after the bending. Alternatively, in an embodiment, at least one first connecting hole is provided in a first region defined by intersecting grooves in the inner marking plate 101, at least one second connecting hole is provided in a second region defined by intersecting grooves in the outer marking plate 102, and each of the first and second connecting holes in the inner marking plate 101 and the outer marking plate 102 is provided with an inner thread that fits with the outer thread of the fixing member of the inner marking plate 101 and the outer marking plate. As shown in FIG. 1, the first and second connecting holes 1020 are provided respectively in the first and second regions formed by intersecting the grooves 1011 and 1012. Thus, the fixing member with the outer thread may fix the inner marking plate 101 and the outer marking plate 102 through the first and second connecting holes 1020 while effectively preventing the image developing tube 103 from shaking due to the restoring force. In addition, since the first and second connecting holes 1020 are provided respectively in the first and second regions formed by intersecting grooves, an outer space structure of the inner marking plate 101 and the outer marking plate 102 may be saved, and an outer size of the marking plate assembly may be reduced.

It should be noted that the number of first and second connecting holes 1020 is only an example, and according to actual needs, only one first and second connecting hole or two or more first or second connecting holes may be provided, which is not limited in the present embodiment.

Based on the marking plate assembly shown in FIGS. 1 to 3, an embodiment of the present disclosure also provides a positioning apparatus for MRI, which includes a three-dimensional frame structure 1 formed by the marking plate assemblies provided in any one of the above embodiments. The number of marking plate assemblies in the three-dimensional frame structure 1 is greater than or equal to 4.

Figure 4:
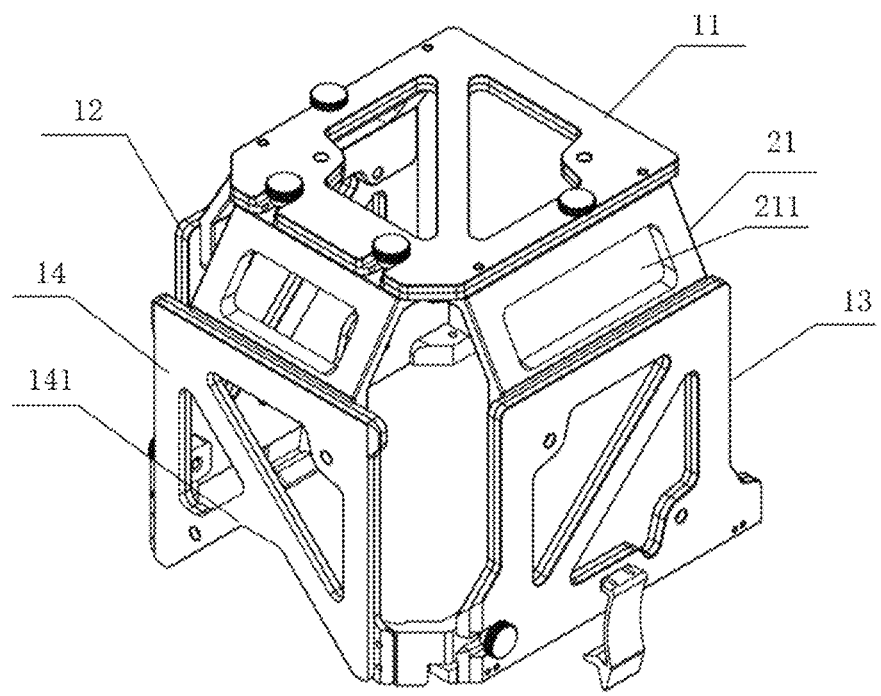
FIG. 4 is a schematic structural diagram of a positioning apparatus for MRI provided in an embodiment of the present disclosure.

For example, in an embodiment, the three-dimensional frame structure 1 is formed by 4 marking plate assemblies. Specifically, as shown in FIG. 4, the three-dimensional frame structure 1 includes a straight upper marking plate assembly 14 configured to cover a face of a patient when in use, a straight left marking plate assembly 12 and a straight right marking plate assembly 13 configured to respectively cover left and right ears of the patient when in use, and a straight front marking plate assembly 11 configured to cover a top of a head of the patient when in use. The straight upper marking plate assembly 14, the straight left marking plate assembly 12, the straight right marking plate assembly 13, and the front marking plane assembly 11 all adopt the marking plate assembly provided in any one of the above embodiments. Since in the marking plate assembly, the developer solution is enclosed in the image developing tube, the image developing tube is arranged in the cavity formed by the groove structure in the inner marking plate and the groove structure in the outer marking plate, so that the positioning apparatus for MRI provided in the present embodiment will not leak the developer solution even if the inner marking plate or the outer marking plate does not meet the process requirements, which improves the use performance of the positioning apparatus for MRI.

In addition, during an MRI scan, the developer solution in the positioning apparatus for MRI is imaged as several dots in tomographic images scanned by the MRI technology. A relationship between these dots may be used to infer a relationship of the scanned tomographic images in a space coordinate system, and an angular deviation and position deviation between the tomographic images may be obtained through calculation. The positioning apparatus for MRI uses this principle to register the tomographic images, and through tomographic reconstruction technology, a three-dimensional model of the MRI-scanned location of a lesion may be accurately obtained. In the present embodiment, the upper, left, right, and front positions of the three-dimensional frame structure 1 are respectively provided with the straight upper marking plate assembly 14, the straight left marking plate assembly 12, the straight right marking plate assembly 13, and the straight front marking plate assembly 11, which allows the positioning apparatus for MRI provided in the present embodiment to acquire a cross-sectional tomographic image covering the top surface of the head, a coronal tomographic image covering the face, and sagittal tomographic images covering the left and right ears. Compared with the three-dimensional frame structure that only includes 3 marking plate assemblies (for example, only including the straight upper marking plate assembly, the straight left marking plate assembly, and the straight right marking plate assembly), it can also realize the scanning of a sagittal plane, and the scanning function is more comprehensive and flexible. Moreover, because the sagittal plane may be scanned, compared with the three-dimensional frame structure that includes only 3 marking plate assemblies, not only can the coronal tomographic image and the cross-sectional tomographic image be used for error correction, but also the sagittal tomographic images can be used for error correction, thereby improving the accuracy of tumor positioning.

For ease of understanding, the process of error correction using the 3 types of tomographic images acquired by the positioning apparatus for MRI provided in the present embodiment will be described in detail below in conjunction with FIG. 5 and FIG. 6.

Figure 5:
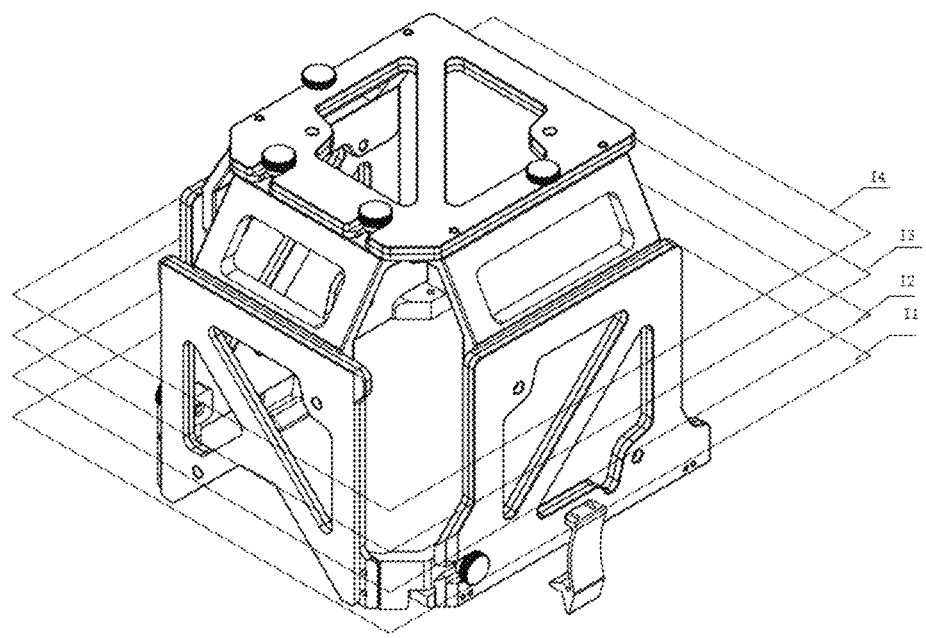
FIG. 5 is a schematic diagram of an MRI tomography scan of the positioning apparatus for MRI provided in an embodiment of the present disclosure.
Figure 6:
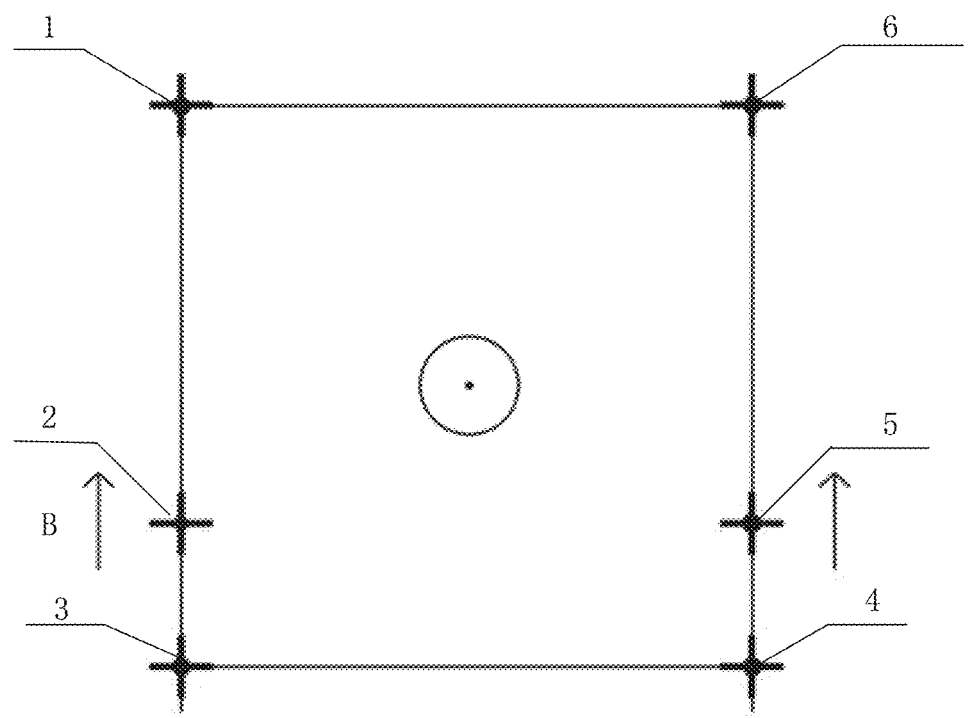
FIG. 6 is a diagram of a positional relationship of a developer solution of the positioning apparatus for MRI in a magnetic resonance tomographic image provided in an embodiment of the present disclosure.

Referring to FIG. 5, the faults I1 to I4 scanned by MRI tomographic scan are parallel to each other and arranged in sequence from bottom to top. The image scanned by the MRI device is a cross-sectional view of each plane shown in FIG. 6. Since the developer solution in the image developing tube is imaged in MRI, the final result is 9 dots. For the convenience of description, FIG. 6 uses 6 dots to illustrate the principle of determining an error. The dots 1, 3, 4, and 6 are the imaging of the image developing tubes perpendicular to the faults I1 to I4 in the left and right marking plate assemblies 12 and 13 in the three-dimensional frame structure 1, and the dots 2 and 5 are the imaging of the image developing tubes arranged obliquely in the left and right marking plate assemblies 12 and 13 in the three-dimensional frame structure 1. Because a distance between the images of the tomographic scan is fixed, and the image developing tube arranged in an oblique direction is arranged at an angle of 45°, the positions of the dots 2 and 5 in different faults are also different, and their displacement is related to the distance between two faults, and the relationship is that the distance between the two faults is equal to a distance moved up and down by point 2 or point 5. In the structure shown in FIG. 6, the closer the fault is to the tip, the points 2 and 5 move in a direction B, and the closer to the points 1 and 6.

In specific applications, when performing an MRI scan on the head of the patient, the head of the patient needs to be fixed by a fixing apparatus, which is connected with the positioning apparatus for MRI to keep a relative position between the head of the patient and the positioning apparatus for MRI unchanged. The positioning apparatus for MRI needs to be connected to a treatment couch of the magnetic resonance equipment, and be sent into the magnetic resonance equipment along with the treatment couch. Because in an initial positioning stage, the MRI equipment, the positioning apparatus for MRI, and the head of the patient may not be able to maintain a relatively accurate position (for example, there are some human errors), and there may also be some slight errors in the treatment couch, the accumulation of these two quasi-errors may interfere with the subsequent tumor positioning work. In order to eliminate the influence of this part of the error, the magnitude of various errors may be determined based on the changes of the dots of the tomographic images, for example, when the distance between any faults is not equal to a longitudinal movement distance of point 2 or point 5, there is a linear deviation in the patient's body orientation, and a deviation value is equal to a difference between the movement distance of the point and the distance between the faults. When the positions of points 1, 3, 4, and 6 in different tomographic images change, there is a certain angular deviation in the patient's body orientation. Using the positioning apparatus for MRI provided in the present embodiment, three sets of such data may be obtained. Compared with the positioning apparatus for MRI without the straight front marking plate assembly 14 in the related art, one extra set of data may be compared with the other two sets of data, to avoid accidental errors and improve the accuracy of tumor positioning.

Alternatively, in other embodiments, the three-dimensional frame structure 1 may also be formed by 5 marking plate assemblies, that is, in addition to the straight upper marking plate assembly 14, the straight left marking plate assembly 12, the straight right marking plate assembly 13, and the straight front marking plate assembly 11, the marking plate assemblies also includes a lower marking plate assembly (not shown) arranged in parallel with the straight upper marking plate assembly 14 to increase the stability of the positioning apparatus for MRI.

Since a posterior marking plate is usually located at the back brain of the patient, during MRI scan, the head of the patient needs to wear a positioning apparatus (head frame or mask assembly), and then wear the three-dimensional frame structure of the present disclosure outside the positioning apparatus, and finally wear an adapter for MRI outside the three-dimensional frame structure to be fixedly connected to a positioning interface on a scanning couch. Therefore, the setting of the posterior marking plate may affect the installation and positioning accuracy of an entire scanning positioning accessory, and make the entire three-dimensional frame structure more complicated. Therefore, preferably, the three-dimensional frame structure includes 4 marking plate assemblies, namely, the straight upper marking plate assembly 14, the straight left marking plate assembly 12, the straight right marking plate assembly 13, and the straight front marking plate assembly 11.

It should be noted that, in order to provide comfort, as shown in FIG. 4, an inverted V-shaped opening 141 is provided under the straight upper marking plate assembly 14, and the inverted V-shaped opening 141 under the straight upper marking plate is located in front of the nose of the patient during use, providing an open space for the patient.

It should be noted that, in order to increase an internal space of the three-dimensional frame structure 1, as shown in FIG. 4, the three-dimensional frame structure 1 further includes connecting plates 21, and the connecting plates 21 are arranged between the straight front marking plate assembly 11 and other marking plate assemblies for fixedly connecting the straight front marking plate assembly 11 with the other marking plate assemblies. In the present embodiment, specifically, the connecting plates 21 are provided between the straight front marking plate assembly 11 and the straight left marking plate assembly 12 and between the straight front marking plate assembly 11 and the straight right marking plate assembly 13. Alternatively, the connecting plate 21 has a cuboid structure, and a rectangular through hole 211 is provided at a center position of the connecting plate 21. By providing the rectangular through hole, the weight of the connecting plate 21 may be reduced, thereby reducing the weight of the three-dimensional frame apparatus.

It should be noted that when the positioning apparatus for MRI includes the lower marking plate assembly, a connecting plate for connecting the straight front marking plate assembly 11 and the lower marking plate assembly needs to be correspondingly provided. The structure, function, and connection method of the connecting plate are the same as those of the connecting plate 21 used to connect the straight front marking plate assembly 11 and the other marking plate assemblies, and detailed description thereof will be omitted.

The embodiments in this specification are described in a progressive method, and the same or similar parts between the embodiments may refer to each other. Each embodiment focuses on the differences from other embodiments. Specifically, for the system embodiment, since it is basically similar to the method embodiment, the description thereof is relatively simple. For related details, reference may be made to the part of description in the method embodiment.

The above description is merely embodiments of the present disclosure and is not intended to limit the present disclosure. For those skilled in the art, the present disclosure may have various modifications and changes. Any modification, equivalent replacement, improvement, etc. made within the spirit and principle of the present disclosure shall be included in the scope of the claims of the present disclosure.

What is claimed is:

1. A positioning apparatus for magnetic resonance imaging, comprising a three-dimensional frame structure formed by marking plate assemblies, each of the marking plate assemblies comprising an inner marking plate, an outer marking plate arranged opposite to the inner marking plate, and an image developing tube in which a developer solution is enclosed, opposite surfaces of the inner marking plate and the outer marking plate being respectively provided with groove structures, the image developing tube being arranged in a cavity formed by the groove structure in the inner marking plate and the groove structure in the outer marking plate, and a number of the marking plate assemblies being greater than or equal to 4.

2. The apparatus according to claim 1, wherein the image developing tube is a plastic hose with a preset hardness, and the preset hardness ranges from 45A to 85A.

3. The apparatus according to claim 2, wherein the preset hardness is 65A.

4. The apparatus according to claim 1, wherein two ends of the image developing tube are respectively provided with plugs, and the plugs are sealed together with the image developing tube through a thermoplastic process.

5. The apparatus according to claim 4, wherein at least one of the plugs is closely fitted in the image developing tube.

6. The apparatus according to claim 5, wherein the inner marking plate and the outer marking plate are connected by a fixing member with an outer thread.

7. The apparatus according to claim 6, wherein the groove structure in the inner marking plate and the groove structure in the outer marking plate respectively comprise grooves arranged along an edge and a diagonal direction of the inner marking plate, and grooves arranged along an edge and a diagonal direction of the outer marking plate.

8. The apparatus according to claim 7, wherein the groove structure further comprises a groove extension part arranged along the diagonal direction at a position where the grooves intersect, and the image developing tube is bent at the position where the grooves intersect so that the two ends of the image developing tube are arranged in the groove extension part.

9. The apparatus according to claim 7, wherein at least one first connecting hole is provided in a first region defined by intersecting grooves in the inner marking plate, at least one second connecting hole is provided in a second region defined by intersecting grooves in the outer marking plate, and each of the first and second connecting holes in the first and second regions is provided with an inner thread that fits with the outer thread of the fixing member.

10. The apparatus according to claim 1, wherein the inner marking plate and the outer marking plate are detachably connected.

11. The apparatus according to claim 1, wherein the developer solution comprises one of following materials: a copper sulfate solution, glycerin, and a nitrate oil solution.

12. The apparatus according to claim 1, wherein the marking plate assemblies comprise a straight upper marking plate assembly configured to cover a face of a patient when in use, a straight left marking plate assembly and a straight right marking plate assembly configured to respectively cover left and right ears of the patient when in use, and a straight front marking plate assembly configured to cover a top of a head of the patient when in use.

13. The apparatus according to claim 12, wherein an inverted V-shaped opening is provided under the straight upper marking plate assembly.

14. The apparatus according to claim 12, wherein the marking plate assemblies further comprise a lower marking plate assembly arranged in parallel with the straight upper marking plate assembly.

15. The apparatus according to claim 12, wherein the three-dimensional frame structure further comprises connecting plates, and the connecting plates are arranged between the straight front marking plate assembly and other marking plate assemblies for fixedly connecting the straight front marking plate assembly with the other marking plate assemblies.

16. The apparatus according to claim 15, wherein each of the connecting plate has a cuboid structure, and a through hole is provided at a center position of the connecting plate.

* * * * *